United States Patent [19]

Eberhard et al.

[11] 4,333,473
[45] Jun. 8, 1982

[54] APPARATUS FOR THE CUTANEOUS DETERMINATION OF THE OXYGEN PARTIAL PRESSURE IN BLOOD

[75] Inventors: Patrick Eberhard, Allschwil; Wolfgang Mindt, Münchenstein, both of Switzerland

[73] Assignee: Hoffmann-La Roche Inc., Nutley, N.J.

[21] Appl. No.: 72,367

[22] Filed: Sep. 5, 1979

[30] Foreign Application Priority Data

Sep. 11, 1978 [CH] Switzerland .................. 9488/78

[51] Int. Cl.³ .............................................. A61B 5/00
[52] U.S. Cl. ............................ 128/635; 204/195 B; 204/195 P
[58] Field of Search .................. 128/635; 204/195 B, 204/195 P

[56] References Cited

U.S. PATENT DOCUMENTS

| Re. 30,317 | 7/1980 | Lubbers et al. | 128/635 |
| 3,985,633 | 10/1966 | Lubbers et al. | 128/635 |
| 4,094,305 | 6/1978 | Kessler | 128/635 |
| 4,197,853 | 4/1980 | Parker | 128/635 |

OTHER PUBLICATIONS

Eberhard et al., "An Introduction to Cutaneous $O_2$ Monitoring . . . ", Roche, Bio-Electronics, 1976, pp. 1-34.

Primary Examiner—Lee S. Cohen
Attorney, Agent, or Firm—Jon S. Saxe; George M. Gould; John J. Maitner

[57] ABSTRACT

An apparatus for the simultaneous determination of the cutaneous blood gas concentration and of the blood gas availability for the correction of physiologically caused errors of the measured value of the cutaneous blood gas concentration by means of two heated blood gas electrodes in structural unity, of which one is distinguished by maximum gas consumption.

2 Claims, 2 Drawing Figures

APPARATUS FOR THE CUTANEOUS DETERMINATION OF THE OXYGEN PARTIAL PRESSURE IN BLOOD

BACKGROUND OF THE INVENTION

The invention is concerned with an apparatus for the cutaneous determination of the partial pressure of gases in blood with a heated polarographic blood gas electrode and an arrangement for the determination of the blood gas availability at the contact surface. The term "cutaneous" used herein denotes a bloodless measurement recording by a an electrochemical sensor placed on the skin.

It is well known that the $pO_2$-value measured with heated cutaneous oxygen electrodes does not always correlate with the arterial $pO_2$-value, since other parameters such as, for example, the microcirculation, diffusion resistance of the skin and the circulatory condition can also influence the cutaneous $pO_2$-value. Thus, for example, some medicaments which have vasodilating or vasoconstricting activity, used in intensive care cause fluctuations in the cutaneous $pO_2$-value while the central-arterial $pO_2$-value remains constant. Likewise, it is known that fluctuations in the blood pressure (especially in the case of patients with a variable circulatory condition) can influence the cutaneous $pO_2$-value. For these reasons a satisfactory interpretation of the cutaneous $pO_2$-value is not always possible. This restriction has contributed materially to the fact that the method for cutaneous $pO_2$-measurement in the supervision of adult intensive care patients has hitherto not succeeded.

Experiments have already been carried out to couple a perfusion measurement with the cutaneous $pO_2$-measurement in order to enable an improved interpretation of the cutaneous $pO_2$-value. This has hitherto exclusively been carried out using methods which rely on the determination of the heat transport at the measurement position. The method described by Lubbers and coworkers, U.S. Pat. No. 3,918,434, relies on the measurement of the heat energy which is required to heat the oxygen electrode to a constant temperature. With increased local perfusion a greater heat energy is consumed. One disadvantage of this method is, however, that only a small heat energy (according to recently published estimates 25%) is removed by the blood flow. The rest of the heat energy is used to heat non-perfused tissues as well as the surroundings of the electrode. For this reason the method according to Lubbers et al. is relatively unsensitive and, moreover, requires a high expenditure for the heat isolation of the electrode against the surroundings. It is, however, accepted that in principle the validity of the cutaneous $pO_2$-observation is increased by a simultaneous measurement of the perfusion.

Apart from the method described by Lubbers by determining the heat energy for the maintenance of a constant temperature at the measurement position there are still other methods which rely on the measurement of the heat transport. Another method consists, for example, in applying heat at one position and measuring the temperature at a second position situated at a determined distance therefrom. The temperature difference produced is likewise a measurement of the perfusion.

The previous discussions of the state of the art relate almost exclusively to the measurement of the $pO_2$ in blood. This is attributed to the fact that until now only the $pO_2$-measurement has found acceptance in clinical practice. It is, however, known to the person skilled in the art that the partial pressure of other blood gases, especially the $pCO_2$, can be measured in principally the same manner. In so doing, such measurements can be carried out either separately or combined with one another. With regard to this, the present invention is not limited to the measurement of a particular blood gas concentration; it can be used not only in the measurement of $pO_2$ but also of other gases in blood which are to be determined electro-chemically, especially the $pCO_2$.

SUMMARY OF THE INVENTION

The aim of the present invention is to provide an improved method for the simultaneous cutaneous measurement of the partial pressure of a gas in blood and the perfusion, which does not have the disadvantages of the known methods, i.e. which can be carried out with especially higher accuracy.

In accordance with the present invention the foregoing aim is achieved in that the arrangement for the determination of the blood gas availability includes a second polarographic electrode with maximum regular gas consumption in structural unity with the first polarographic blood gas electrode.

As already mentioned, the correlation of the cutaneous measured blood gas value with the actual arterial value can be observed with such an electrode arrangement, in that the measurement value for the gas availability at the contact surface can serve for the interpretation of the measured concentration values. In other words, a correction factor for the measurement value of the cutaneous $pO_2$ can be determined from the measurement value of the gas availability. Moreover, the simultaneously measured value of the gas availability can serve as the function control for the apparatus. Thus, for example, errors in the application such as the use of too much contact gel, the detachment of the sensor, the presence of air bubbles between the skin and the sensor, burn blisters and other skin damage etc, can be detected. On the other hand, variations in the circulatory activity can be included in the safeguarding of accurate functions. In particular, the effects of medicaments on the circulation can be included so that, inter alia, their influence on the measurement of the blood gas circulation can be taken into consideration. Finally, above all in the case of neonates in which usually no influence of medicaments is present, a qualitative observation of the blood pressure is possible using the measurement of the gas availability, which is also dependent on the blood pressure.

BRIEF DESCRIPTION OF THE DRAWING

An embodiment of the present invention is described hereinafter in connection with the accompanying drawing, in which.

DESCRIPTION OF THE PREFERRED EMBODIMENT

Figure 1A:
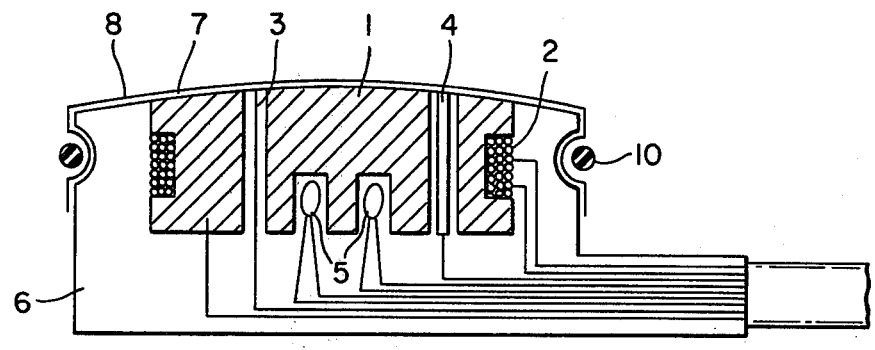
FIG. 1A illustrates in a cross-sectional side view the depicted embodiment of the invention.
Figure 1B:
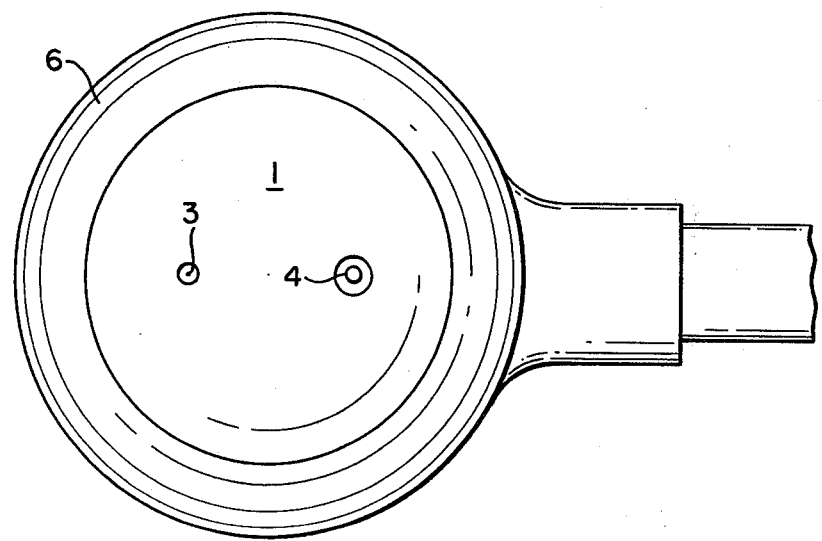
FIG. 1B illustrates a view of the contact surface of the device of FIG. 1A without a membrane.

FIG. 1A shows a section through an oxygen electrode according to this invention and thereunder a view of the contact surface without a membrane.

In this embodiment, an essentially cylindrical silver electrode 1 is provided with a heating arrangement. The surface of the silver electrode 1 has a circular recess in which is situated a heating coil 2. Two eccentric concentrically arranged continuous bores in the silver electrode serve for the reception of two platinum electrodes 3 and 4. The ends of the platinum electrodes lie in one plane with the corresponding face of the silver electrode. One of the two platinum electrodes, i.e. electrode 3, consists of very thin platinum wire and has a diameter of about 25 μm. The other platinum electrode 4 consists of a platinum pin of ca 2 mm diameter. The side lying opposite this face carries two further borings in the silver block in which are situated in each case a temperature measuring element 5.

Instead of platinum, the electrode material may be another precious metal (e.g. gold) which is customary in the case of polarographic electrodes.

All conductors are led away laterally and connected into a cable (not particularly shown). The entire arrangement is surrounded with a flat-cylindrical capsule 6 of synthetic material, one face of the capsule leaving the electrodes free. For the measurement, the face is coated with an electrolyte film 7 and covered with a membrane 8 which is held by an elastic O-ring 10. The membrane consists of polytetrafluoroethylene (Teflon) of 25 μm thickness. The membrane can consist of other materials and thicknesses. It is only important that the membrane must be relatively well permeable for oxygen.

In operation, the electrodes are connected so that the two platinum electrodes 3 and 4 serve as cathodes, while the silver electrode 1 serves as the anode. The microcathode 3, which has a diameter of ca 25 μm, possesses a very much lower oxygen consumption. It is consequently suitable for the measurement of the oxygen partial pressure. The large-surface cathode 4, which has a diameter of ca 2 mm, accordingly consumes practically the entire oxygen arriving at the contact surface. Consequently, it can serve for the determination of the oxygen availability. In this manner there can also be obtained, simultaneously with the cutaneous $pO_2$-measurement, a prediction concerning the blood perfusion in the surroundings of the measurement position. The advantage of the oxygen-flow measurement vis-a-vis the heat-flow measurements used hitherto in this connection consists in that the perfusion measurement is not disturbed by removal of heat in the surroundings. No expensive thermal isolation of the measurement arrangement is therefore necessary. Moreover, the measurement of the oxygen flow has a higher sensitivity.

In addition to the previously described preferred embodiment of the invention, other embodiments with various constructive solutions are also conceivable. Thus, for example, the heating can be arranged, instead of at the anode, at the large-surface cathode 4 which, for this purpose, would be appropriately enlarged.

Another possibility consists in providing a heating element independent of the electrodes.

A further possibility, to obtain the differentially high oxygen consumption of the two cathodes, consists in providing two similarly sized so-called macrocathodes and to cover these with differentially permeable membranes. The one of the two cathodes, which serves for the perfusion measurement, can have a Teflon membrane whose permeability is high, while the other cathode, which serves for the $pO_2$-measurement, must be covered with a relatively less permeable membrane (e.g. Mylar). This arrangement would tend to be more complicated regarding construction and application than the previously described preferred embodiment.

We claim:

1. An apparatus for the cutaneous determination of the partial pressure of gases in blood comprising an anode having a contact surface for application to an individual's skin; a first cathode being a blood gas electrode having a first contact surface for application to an individual's skin and having a gas consumption sufficiently low to enable representative partial pressure measurements; a second cathode being a second blood gas electrode having a second contact surface and consuming practically all gas arriving at its contact surface, the two cathode electrodes being in structural unity with the anode to form a common contact surface; a membrane covering said common contact surface for the application to an individual's skin, and a heating means for heating the common contact surface for thermal stimulation of the blood perfusion.

2. An apparatus according to claim 1, wherein the first blood gas electrode is a so-called microcathode and the second blood gas electrode is a large-surface cathode.

* * * * *